(12) United States Patent
Cummings

(10) Patent No.: US 6,555,359 B2
(45) Date of Patent: Apr. 29, 2003

(54) PROCESS FOR THE ANAEROBIC TREATMENT OF FLOWABLE AND NONFLOWABLE ORGANIC WASTE

(75) Inventor: Robert J. Cummings, Spencer, NY (US)

(73) Assignee: Anaerobics, Inc., Aurora, NY (US)

( * ) Notice: Subject to any disclaimer, the term of this patent is extended or adjusted under 35 U.S.C. 154(b) by 0 days.

(21) Appl. No.: 09/962,394

(22) Filed: Sep. 25, 2001

(65) Prior Publication Data

US 2003/0059927 A1 Mar. 27, 2003

(51) Int. Cl.⁷ .......................... C07G 17/00; C12M 1/00; C02F 3/00
(52) U.S. Cl. ................. 435/267; 435/293.1; 435/290.4; 435/801; 210/603; 210/608; 210/617; 210/218
(58) Field of Search ................. 210/603, 608, 210/194, 218, 539, 617, 618; 435/293.1, 299.1, 801, 290.4

(56) References Cited

U.S. PATENT DOCUMENTS 4,334,997 A * 6/1982 Peterson ................. 210/603
4,735,724 A 4/1988 Chynoweth et al.
5,733,454 A 3/1998 Cummings
5,773,526 A * 6/1998 Van Dijk et al. ........... 210/603

* cited by examiner

Primary Examiner—David A. Redding
(74) Attorney, Agent, or Firm—Stephen B. Salai, Esq.; Roger Aceto, Esq.; Harter, Secrest & Emery LLP

(57) ABSTRACT

A method and apparatus for anaerobic treatment of organic wastes in a liquid filled vessel wherein particles of the waste are buoyed and form a floating bed in the liquid by the gasses generated by the anaerobic digestion of the wastes. The bed forms to an upper stratum of the least digested, least dense waste and a lower stratum of the most digested, most dense waste. Liquid from beneath the bed is continuously sprayed over the upper surface of the bed through a series of discharge ports which expands to bed downwardly. Each spraying period is followed by a quiescent period to allow the bed to reform. Over time the floating bed is moved from an inlet end to an outlet end of the vessel where the most digested waste is removed.

25 Claims, 2 Drawing Sheets

PROCESS FOR THE ANAEROBIC TREATMENT OF FLOWABLE AND NONFLOWABLE ORGANIC WASTE

FIELD OF THE INVENTION

The present invention relates generally to the treatment of flowable and non-flowable organic waste, and in particular to achieving the efficient treatment of both wastes simultaneously, by anaerobic digestion using a floating bed process and apparatus.

BACKGROUND OF THE INVENTION

It is known that solid (non-flowable) and fluid (flowable) organic wastes may be treated using anaerobic microbiological treatment processes. Various anaerobic systems have been developed to implement the anaerobic digestion of organic wastes. These systems typically work on fluid wastes and slurries and employ a sludge blanket containing the treating bacteria wherein the fluid waste to be treated passes upwardly through the sludge blanket. In these systems the greatest concentration of bacteria is at the bottom of the sludge blanket and least near the top of the sludge blanket. In these systems, at least a portion of the waste stream passing up through the sludge blanket is drawn off and reintroduced below the sludge blanket for another pass up through the blanket. These systems are inefficient for a number of reasons and are ineffective for the treatment of solid nonflowable materials.

The management of organic nonflowable waste materials is a particular concern in the food processing industry as well as within municipalities. In the food processing industry there are large accumulations of vegetable matter from food processing operations such as the husks and cobs remaining after corn is canned or frozen and pea shells remaining after canning or freezing peas. The organic fraction of municipal solid waste, lawn and garden wastes, animal manure, mixtures of the above, and others also occupy large volumes in landfills and are noxious odor concerns. Moreover, extreme environmental contamination may occur when rainwater leaches through such materials and flows into waterways, drinking water supplies and ground waters.

Several means of management and disposal have been attempted including land filling, incineration, use as fertilizer, soil conditioner, animal feeds, and others. However, none of these alternatives have found wide spread practice for many reasons.

Nonflowable organic wastes have one thing in common, which is consistently valuable. They are biodegradable and renewable. If the solar energy contained within these materials could be liberated and captured, a renewable energy source could be derived, while simultaneously eliminating a costly environmental problem.

Nonflowable wastes also are lighter than water and, in the presence of anaerobic microorganisms, produce tiny carbon dioxide and methane gas bubbles which further enhance the capability of these waste materials to float in the presence of water. It is conceivable to develop a floating bed of organic waste within a vessel containing a liquid seeded with anaerobic bacteria. When the liquid is passed through the bed, the bed will filter and entrap the bacteria within the float layer. The solids in the bed also will serve as the media on which these microorganisms can attach themselves. Such a floating bed would have the capability to digest the non-flowable organic material within the bed and simultaneously treat a wastewater containing biodegradable organic material passing through the floating bed. Thus, a floating organic bed reactor can simultaneously treat both flowable and non-flowable waste streams to convert the biodegradable organic material to energy as biogas, reduce the volume of non-flowable waste and remove pollutants from flowable waste streams.

Accordingly, it is an object of the present invention to provide a system for treating both liquid and solid organic wastes.

Another object of the present invention is to provide a system for the biological treatment of both liquid and solids waste streams.

A further object of the invention is to provide a system for the anaerobic treatment of organic liquid and solid wastes.

Yet another object of the present invention is to provide a system for the anaerobic treatment of organic liquid and solid wastes in a common treatment vessel.

Still another object of the present invention is to provide a method and apparatus for the anaerobic treatment of organic and solid wastes in a common treatment vessel utilizing floating bed technology.

Another object of the present patent is to produce energy from the co-digestion of the flowable and non-flowable wastes.

Still another objective of the patent is to reduce the volume of non-flowable organic waste through its conversion to energy and to treat contaminated wastewater, converting its biodegradable organic fractions to energy and leaving treated wastewater for discharge to the environment.

SUMMARY OF THE INVENTION

Briefly stated, the present invention comprises a process and apparatus for the anaerobic biological treatment of liquid (flowable) and solid (nonflowable) wastes in a closed bioreactor vessel. Both solids and liquid wastes are introduced into the vessel at an inlet end and pass longitudinally through the vessel. In transit and while in the vessel, the wastes are contacted with anaerobic microorganisms. These organisms digest the organic matter and the product of the digestion is removed from an opposite end of the vessel. The action of the microorganisms on the organic matter, which is lighter than water, generates gases, such as methane and carbon dioxide, which assist to buoy the organic solids causing them to form a floating bed of solids. The anaerobic microorganisms attach to the organic solids and become entrapped within the floating bed.

As digestion proceeds, particle size of the solid waste is reduced and the density of the material increases. Over time, and as more solids are added to the vessel, a gradient develops within the bed wherein the least digested, least dense material locates in an upper stratum of the bed and the most digested, most dense material locates towards the bottom of the bed. As the most buoyant and least digested material gathers at the upper surface of the bed, the concentration of solids in a given volume of the upper stratum increases relative to the moisture content of that volume. Should the percentage of moisture in any given volume of the bed fall below about 70% the activity of the microorganism is inhibited. Accordingly it is important to maintain the moisture content of the upper stratum of the floating bed and to seed the upper stratum with a liquid rich in anaerobic microorganisms.

Maintaining the upper stratum of the bed properly moisturized preferably is accomplished by drawing a liquid component from the bottom of the vessel and continuously sparging it over the surface of the bed. This not only maintains the upper stratum of the bed properly moisturized, but also the liquid that percolates down through the bed works to maintain a nutrient field throughout the depth of the bed. Sparging, while continuous, does not occur simultaneously over the entire surface of the bed. Instead sparging proceeds in steps across the bed front to back or across the width of the bed. In this respect liquid first is introduced so as to spray over a first portion of the bed located adjacent a front wall of the vessel for a given period of time. Prior to the termination of the spray over the first portion of the bed, a spray over a second adjacent portion of the bed farther from the front wall is started. The first spray is terminated and after a period of time the introduction of liquid begins over a third portion still farther from the front wall. The second spray then is terminated and after a period of spraying only over the third portion, the introduction of liquid begins over a fourth portion of the bed still farther from the front wall. This process continues across the vessel from front to back and repeats.

Each period of liquid introduction is followed by a quiescent period before liquid again is sprayed over a given portion. Depending upon the width of the bed the spraying of liquid over a first portion of the bed adjacent the front wall may recommence before the sequence has reached the last portion of the bed adjacent the back wall of the vessel.

Periodically, the most digested matter in the floating bed adjacent the outlet end is removed from the vessel along with a quantity of liquid. As digestion proceeds, fresh or untreated solid waste is introduced at an inlet end of the vessel opposite from the outlet end. With each successive removal of the most digested matter from the outlet end and introduction of fresh material at the opposite inlet end, the floating bed moves slightly towards the outlet end of the vessel. Over time, the entire floating bed migrates to the outlet end and is digested in transit. The gasses generated by the digestion process collect at the top of the vessel and also are removed and collected for use as an energy source.

Untreated liquids such as municipal wastewater, wastewater from a food processing operation or leachate from a vegetable storage pile or the like, also is introduced into the inlet end of the vessel to replace liquid that is removed from the outlet end. It should be appreciated that a vegetable processing operation generates a large quantity of wastewater. For example, washing vegetables prior to processing produces wastewater that contains vegetable matter and must be treated before discharge to the environment. Also, water leaching from vegetable stockpiles awaiting processing or leaching from stores of processing residue contains a high level of nutrients and must be treated prior to discharge. Wastewater and leachate often are collected in lagoons and treated by aeration prior to discharge. However, both of these liquid waste streams are treatable according to the method and apparatus of the present invention thereby reducing or eliminating the need for aeration. Further, these liquid waste streams can be used to provide a nutrient lagoon for the anaerobic microorganisms within the closed vessel at start up.

In accordance with the present invention, such liquid is introduced into and mixed with the liquid stream that is sprayed over the top of the floating bed. As the liquid mixture passes downwardly through the bed it undergoes treatment by the bacteria within the bed so that by the time the liquid is cycled to the outlet end of the vessel a substantial portion, if not all, of its organic should be digested. Accordingly, the organic material contained by the wastewater component also is treated and digested in transit through the vessel.

Thus, the present invention provides for the treatment of both solid and liquid wastes in a clean, efficient disposal operation, which reduces the volume of the biomass by anaerobic digestion so as to facilitate disposal. The invention further provides for the generation of energy in the form of methane gas that can be sold or used as the energy source for the process.

Accordingly, the present invention may be characterized in one aspect thereof by a process for the biological treatment of liquid and solid organic wastes comprising:

a) contacting organic solids in a vessel with a liquid containing anaerobic microorganisms, the solids forming particles for supporting and entrapping the bacteria and the solids being digested by the microorganisms and being buoyed in the liquid by the gases generated during such digestion so as to form a floating bed wherein an upper stratum of the bed contains the least digested and least dense material and a lower stratum of the bed contains the most digested and densest material;

b) circulating liquid from beneath the floating bed to the upper surface of the floating bed and allowing the liquid to percolate down through the bed;

c) moving the floating bed from an inlet end of the vessel to an opposite outlet end of the vessel; and d) removing the most digested, most dense material from the vessel at the outlet end.

In yet another aspect, the present invention may be characterized by an apparatus for the biological treatment of liquid and solid organic wastes comprising:

a) a closed vessel containing an anaerobic microorganism-rich liquid for conducting the anaerobic digestion of organic matter, the vessel having an inlet at one end for introducing the organic matter to be digested into the vessel and an outlet at an opposite end for removing digested organic matter from the vessel, the organic matter forming a floating bed within the vessel having the densest most digested material in a lower stratum of the bed and the lightest least digested material in an upper stratum of the bed;

b) means for withdrawing liquid from beneath the floating bed and sparging the removed liquid over an upper surface of the floating bed;

c) means for moving the floating bed from the inlet end to the outlet end; and d) means for removing the densest most digested material from the vessel at the outlet end.

DETAILED DESCRIPTION OF THE INVENTION

Figure 1:
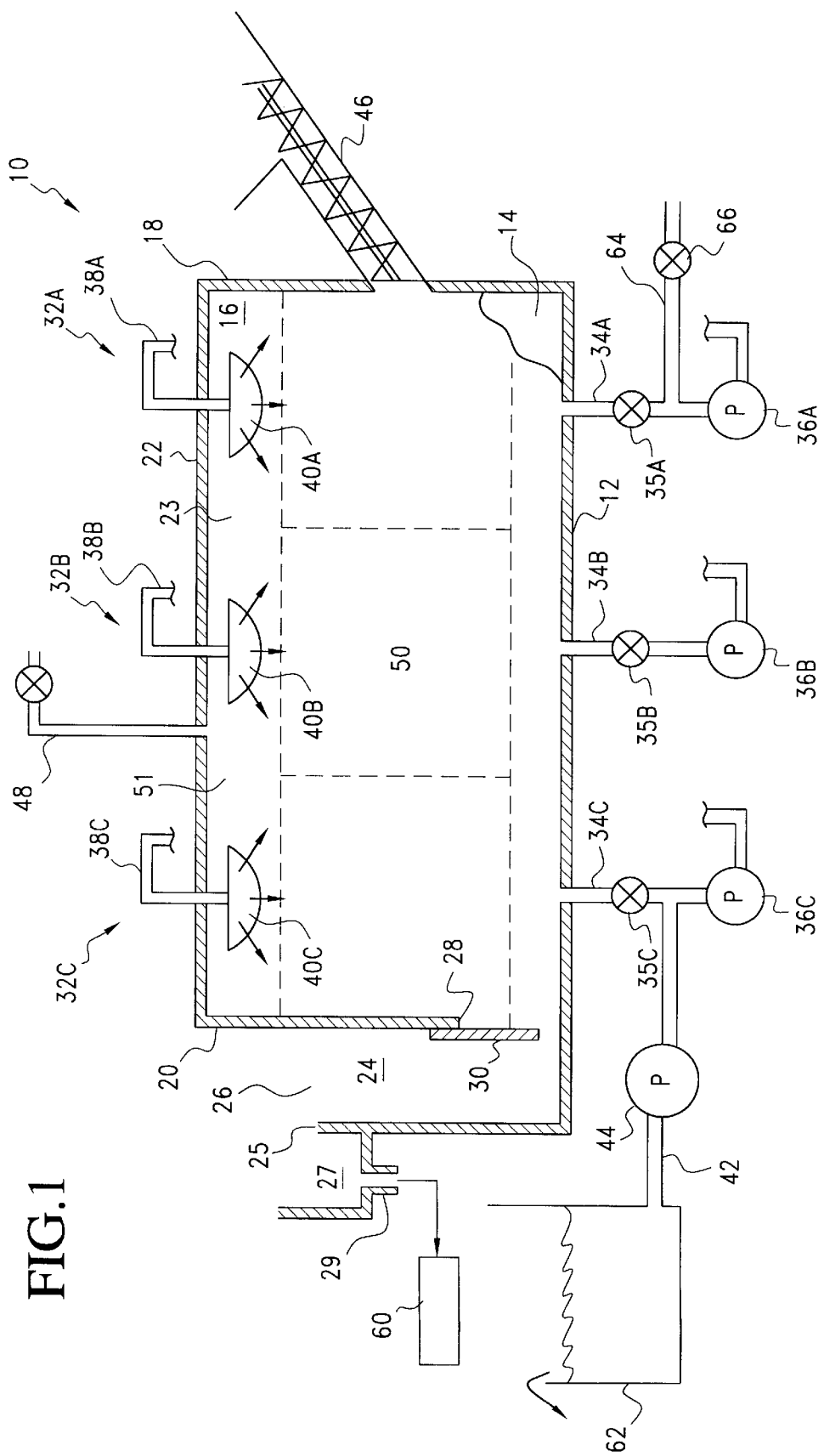
FIG. 1 is a front elevation view of a waste treatment vessel.

Referring to the drawings, FIG. 1 shows a schematic representation of a tank, generally indicated at 10, for conducting an anaerobic digestion of organic solids and the organic fraction of a liquid in accordance with the method of the present invention. Given the quantities of organic material that is processed, the tank, preferably is a relatively large in-ground concrete structure. For example, it may be 240 feet long, 60 feet wide and 20 feet deep.

The tank is a closed bioreactor vessel having a bottom 12, front and rear walls 14 and 16 respectively, end walls 18, 20 and a top 22. Together, the bottom, sides, end walls and top of the tank define a closed process chamber 23 in which an anaerobic digestion process according to the present invention is carried out. As viewed in FIG. 1, the right side represented by end wall 18 is an inlet end of the chamber whereas the left side represented by end wall 20 is an outlet end.

The tank further includes a weir chimney 24 that lies adjacent the outlet end of the vessel. The weir chimney is open at its top 26 and is in communication with the closed process chamber 23 through an opening 28 adjacent the bottom of end wall 20 at the outlet end of the vessel. A gate 30 may be raised and lowered to open and close the passage 28 for purposes set out hereinbelow. Liquid in the chimney overflows the top of a weir 25 and into a weir box 27. The liquid flows out of the weir box 27 through a bottom drain 29 and into a solids-liquids separator 60 such as a mesh screen filter, a rotary screen separator, press or other device for removing fines and other particulate. The filtered liquid is accumulated in a reservoir 62 for future use as set out hereinbelow whereas the removed solids are collected for use as fertilizer, animal feed or the like.

The reservoir may be 3000 cubic feet or more depending upon the size of the tank 10. Since the liquid in the reservoir has undergone treatment and is relatively free of organic materials, any overflow from the reservoir may be discharged to drain.

The tank 10 includes a plurality of circulation systems arranged to circulate liquid through the process chamber 23. For purposes of illustration, the vessel 10 as shown in the Figures has three circulation systems generally indicated at 32A, 32B and 32C spaced along the length of the vessel. Each of the circulating systems defines a zone extending the width of the vessel or front to back as shown in the Figures. In actual practice, a vessel of the size indicated above would contain a larger number of circulation systems.

Figure 2:
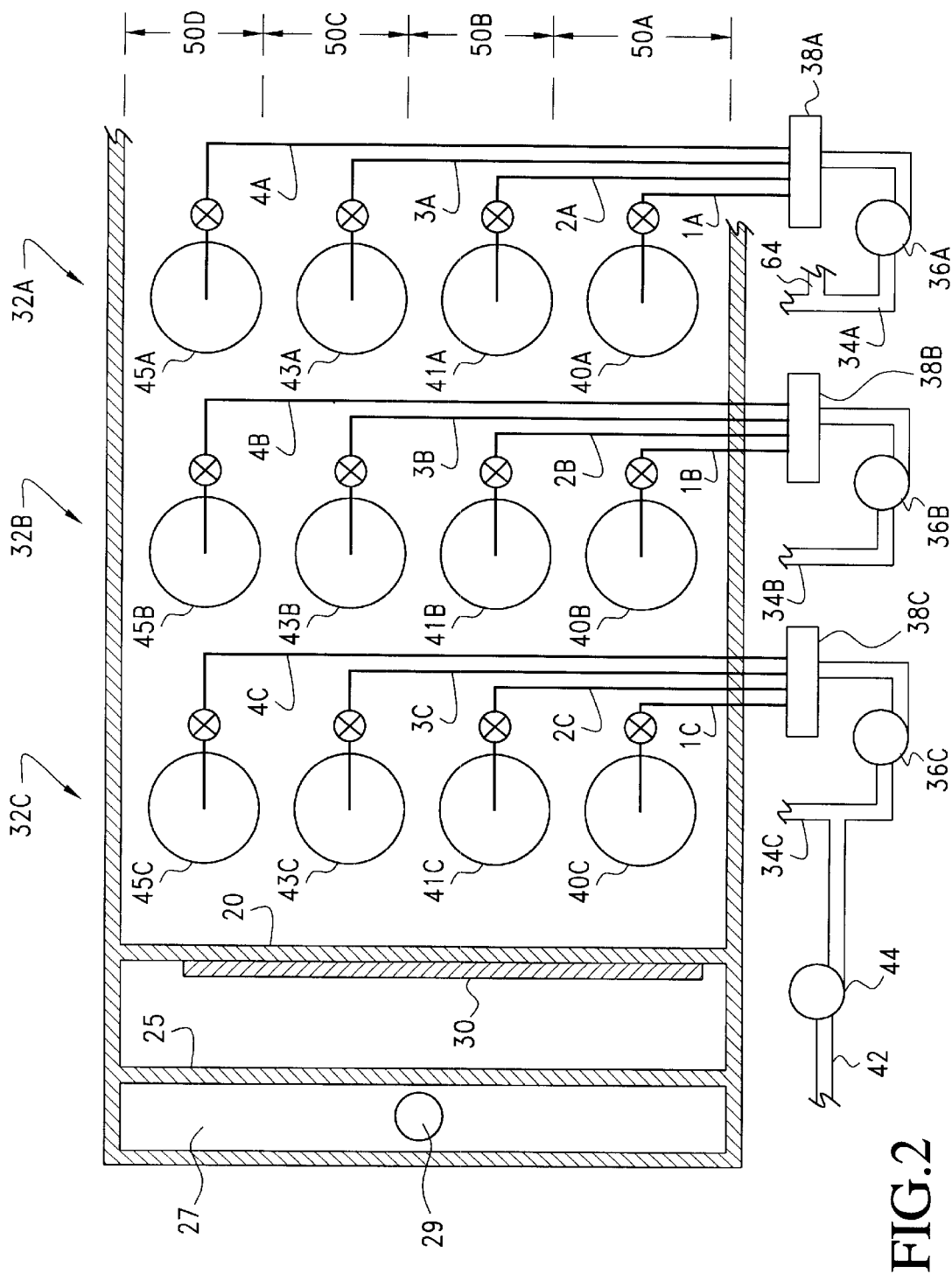
FIG. 2 is a top view of the waste treatment vessel.

The circulation systems are spaced along the length of the tank wherein each system includes an outlet 34 extending through the tank bottom 12. Each outlet 34 is connected to the inlet of a pump 36 so that each outlet 34 comprises a suction outlet for drawing liquid from a given zone in the vessel. The discharge of each pump is connected to a manifold 38 (FIG. 2). Extending from each manifold are a plurality of pipes. The pipes preferably extend along the outside of the tank and enter the process chamber 23 adjacent the top 22 of the tank. FIG. 2 shows that there are four pipes 1, 2, 3 and 4 extending from each manifold. The manifold preferably also is on the outside of the vessel as are each of the pipes 1–4. Running the manifold and pipes along the outside of the tank maintains the process chamber 23 clear of piping for purposes set out hereinbelow. A less preferred construction is to run piping within the vessel but close to and along the bottom and side walls so as to maintain the interior of the vessel substantially clear of piping.

Each pipe extending from the manifold 38 is valved for selectively controlling the flow of liquid through the pipe. Each pipe 1–4 in turn terminates in a distributor 40, 41, 43 and 45 respectively arranged to sparge circulating liquid over a defined, generally circular cross sectional area. The liquid delivered to each of the distributors in any given zone is drawn from the suction outlet 34 in that zone. With this arrangement, liquid removed from one of the zones (as defined by each of the circulation systems) is returned to the zone through the distributors associated with that zone. Accordingly, a substantially vertical flow through the bed occurs wherein the flow is through a generally cylindrical volume. Moreover, the circular areas covered by each distributor overlap at their margins such that substantially the entire cross sectional area of the process chamber may be exposed at one time or another to the shower.

Circulation through each of the systems 32A, B and C, and more particularly through the valved pipes 1, 2, 3 and 4, is controlled by a set of timers (not shown). These timers are programmed to sequence the flow of the circulating liquid through each of the zones. The sequencing begins adjacent the front Wall 14 of the chamber and progresses across the vessel to the rear wall 16. Thus, at the start of the sequence, only the valved pipes 1A, 1B and 1C are open.

The first circulation system 32A as shown in FIG. 1 includes a pipe 64 extending between a source of the untreated liquid and the inlet or suction side of pump 36A. A valve 66 in the pipe 64 controls flow of untreated liquid such as a process wastewater, leachate or the like into the inlet side of the pump 36A. By opening valve 66, a quantity of untreated liquid can be added to the stream circulating through the first circulation system 32A.

The last circulation system 32C includes a connection to the reservoir 62. In this respect a pipe 42 extends from the reservoir to the inlet or suction side of pump 36C. A pump 44 in pipe 42 forces liquid from the reservoir through the pipe 42 to the inlet side of pump 36C at a flow rate that is larger than is normally accommodated by pump 36C. Accordingly, when pump 44 is operating, a variable speed drive (not shown) increases the speed of the pump 36C so it can handle the increased flow.

Passing into the process chamber 23 through the inlet end wall 18 is an influent screw conveyor 46 for delivering an organic solid organic waste to be treated, such as a mass of chopped or comminuted corncobs or other vegetable matter, into the process chamber 23. Completing the structure of the tank 10 is a valved outlet 48 that extends through the top 22 of the vessel for venting gas from the chamber.

At startup, the process chamber 23 is flooded with volume of liquid containing an anaerobic bacterial. Wastewater and leachate containing organic nutrients needed by the anaerobic microorganisms preferably is used in forming the volume of liquid. For example, the wastewater may be from a municipal or industrial source including food processing operations. Leachate may be the collected runoffs from vegetable stockpiles or collections of organic wastes. The liquid is heated to provide the temperature appropriate for growth of the anaerobic bacteria. Heating may be by any suitable means (not shown) including heaters in the circulation systems 32 or by separate steam or hot water lines among others. If needed, the liquid also may be cooled to maintain the proper temperature for anaerobic action.

A quantity of chopped or comminuted solid organic waste such as chopped corncobs and cornhusks or other comminuted vegetable matter is fed into the process chamber 23 through the influent screw conveyor 46. Initially, the organic solids are loaded into the vessel at the rate of about 10 to 20 tons per day or more. Over a period of time and as digestion occurs, a float will develop wherein the solids form a bed 50 that rises to the level of liquid in the process chamber 23 and that floats above the bottom 12 of the tank. In this respect the digestion of the organic solids by the bacteria in the liquid breaks down the organic matter and generates a gas, such as methane, that percolates upwardly through the floating bed. The upward percolation of gas buoys the less dense undigested organic material causing it to float at a higher level of the bed whereas the denser residue of the digestion process sinks to a lower level of the bed. Accordingly, over time a gradient is formed within the bed 50 with the less digested matter in an upper stratum of the bed and most digested matter in a lower stratum of the bed. Moreover, the particles of the organic material act as support particles and the bacteria both attach to these particles and become entrapped between the particles. In this fashion the bacteria remain in intimate contact with the organic particles to facilitate the digestion of the organic solids.

It is known that anaerobic bacteria operate most efficiently in a moist environment. However, due to concentration of the less digested vegetable mass adjacent the upper surface of the floating bed 50, the upper stratum of the bed contains a relatively dry mass of the organic solids. The dryness of this upper stratum inhibits the operation of the anaerobic bacteria. Accordingly, it is important to maintain the upper stratum of the bed in a moistened condition. This is accomplished by the circulation systems 32A–C.

In a steady state operation, the circulation systems 32A–C are operated to shower the upper stratum of the bed to provide a more hospitable environment for the growth of the anaerobic bacteria. As noted hereinabove, the showering of liquid begins along the length of the front wall 14. In this respect, liquid first is drawn from below the floating bed 50 through each of the suction outlets 34A, B and C by the pumps 36A, B and C. The liquid then is pumped through the manifolds 38A, B and C and into the open first valved pipes 1A–C extending from each manifold. This introduces the liquid into the top of the chamber through distributors 40A, B and C. In this fashion, the top of the bed beneath the distributors 40A–C and along the front wall is showered so as to provide a moist, friendly environment for bacteria growth.

The quantity and weight of the liquid discharged through the distributors 40A–C is sufficient to downwardly expand that portion of the bed covered by the liquid. The downward expansion is generally confined to substantially cylindrical volumes wherein the cross sectional area of the cylindrical volumes correspond generally to the areas covered by the distributors 40A–C. While not shown, there preferably is some overlap in the areas covered by the spray from the distributors 40A, B and C. This will insure that a first slice of the bed 50A (FIG. 2) adjacent the front wall and extending the length of the vessel is downwardly expanded.

After a given time, the second valved pipes 2A, B and C are opened and flow is initiated through the distributors 41A–C. For a time all the pipes 1A–C and 2A–C remain open so the flow of liquid causes the downward expansion of a second slice 50B of the floating bed along the length of the vessel. The valved pipes 1A–C then are closed and flow to the distributors 40A–C is terminated which initiates a quiescent period. During this quiescent period, the downwardly expanded volume 50A compacts by floating and reforms at its original level. The downward expansion and subsequent upward compaction of a portion of the bed in this fashion liberates gas from within the bed and allows the liberated gas to percolate upwardly through the bed. The gas liberated in this fashion accumulates in the headspace 51 over the bed. The downward expansion and subsequent upward compaction of the bed also facilitates the distribution of the bacteria through out the bed.

During the quiescent period, portions of the bed adjacent the downwardly expanded volume will tend to flow into the vacated volume. However, the opening of the valved pipes 2A–C to begin the circulation of liquid through the distributors forces the adjacent portion 50B of the bed to expand downwardly so there is a resistance to the flowing of the solids into the adjacent areas during the quiescent period. The valved pipes 1A–C eventually are closed while flow continues through the valved pipes 2A–C.

After a time, valved pipes 3A–C are opened to downwardly expand another slice 50C of the floating bed. Both valved pipes 2A–C and 3A–C remain open for a time before valved pipes 2A–C are closed. The process as setout above repeats with valved pipes 4A–C to downwardly expand the last slice 50D of the bed adjacent the rear wall 16 and then the sequence repeats with the opening of valved pipes 1A–C. Each downward expansion is followed by a quiescent period to allow the expanded portions of the bed to reform.

The liquid showered or sparged over the top of the floating bed percolates down through the floating bed through generally cylindrical volumes. The cross sectional area of each of these volumes corresponds generally to the areas covered by the distributors 40, 41, 43 and 45. Anaerobic bacteria, carried along by this flow are both entrapped in the bed and become attached to the particles of the organic material. Keeping the bacteria in close proximity with the organic solids speeds the digestion of the adjacent vegetable matter.

The residue of the anaerobic digestion has a generally higher specific gravity due to its smaller particle size so this material tends to sink towards the bottom stratum of the bed. Conversely, and as noted above, the undigested vegetable matter in the bed, buoyed by the evolving gas, rises to an upper stratum of the floating bed where it is contacted by the shower from the distributors 40, 41, 53 and 45.

The digestion residue towards the bottom of the bed is not as nutritious as the undigested organic mass at the top of the floating bed so the growth of anaerobic bacteria in the residue is inhibited. Also, the liquid drawn from the bottom of the process chamber 23 below the floating bed contains a much reduced quantity of organic matter than the initial wastewater and leachate so the disposal of this liquid is facilitated.

The initial retention time in the vessel may vary depending upon several factors. However, after an initial period of about 40 to 60 days and preferably in about 60 days the removal of the residue from the process chamber 23 can begin. As further described hereinbelow, the entire floating bed 50 is urged to move horizontally towards the wall 20 at the outlet end of the vessel. Accordingly, not only does the specific gravity of the bed increase from top to bottom, but also from the inlet end to the outlet end. Thus, the material in the bed 50 that lies adjacent the gate 30 is the densest and most digested material of the bed whereas the material at the top of the bed adjacent the wall 18 at the inlet end of the vessel is the least dense and least digested.

To move the floating bed towards the end wall 20, a portion of the most digested material within the circulation zone 32C adjacent the outlet end 20 is removed from the vessel. This may start after about 60 days of the initial loading, it being understood that loading of material into the process chamber 23 can occur at intervals over the initial 60 day period and even daily. The removal of the most digested material is accomplished first by closing the valve 35C to close the suction drain 34C and opening the gate 30. Next, pump 44 is operated to pump liquid from the reservoir 62. The volume of flow through pipe 42 is greater than usually accommodated by pump 36C so the speed of pump 36C is increased to accommodate the additional flow. In addition, all the valved pipes 1C, 2C, 3C and 4C are opened so the circulation system 32C delivers a large quantity of liquid over the top of the portion of the floating bed serviced by the circulation system 32C. This large quantity of liquid downwardly expands a portion of the bed adjacent the end wall 20 and flushes a lower portion of the floating bed adjacent the opening 28 through the opening and into the weir chimney 24. The material of the bed removed from the process chamber 23 by this flushing action comprises the most digested and densest digestion residue.

The liquid and flushed solids rise in the weir chimney 24 and flow over the top 25 of the weir into the weir box 27. From the weir box they flow through drain 29 to the separator 60. Here the solids component is removed and the liquid component is drained into the reservoir 62.

Periodically, a quantity of fresh vegetable matter is introduced through the screw conveyor 48. For example, during a steady state operation, as much as 200 tons/day of fresh vegetable matter may be introduced in batches or continuously at the inlet end. The introduction of fresh matter in this matter moves the floating bed laterally towards the outlet end 20. As noted above, all the piping is external of the vessel 10 so that there is no impediment within the process chamber 23 to the lateral movement of the floating bed.

As noted above, wastewater and leachate as may come from vegetable processing provide nutrients for the anaerobic bacteria. Both liquids can be treated in the process chamber 23 to reduce the organic content of these waste streams prior to discharge. In this respect, wastewater and leachate streams may be used in the initial flooding of the process chamber to form the anaerobic lagoon. Wastewater and leachate also and may be used from time to time to spike the liquid flowing through the first circulation system 32A at the inlet end of the tank. As shown in FIG. 1, a pipe 64 connected to the inlet side of pump 36A is arranged to conduct fresh wastewater and leachate into the circulation system 32A. This is done by opening valve 66 in pipe 64 to allow a desired quantity of fresh wastewater and leachate to mix with the liquid in the first circulating system 32A.

As the wastewater and leachate received from pipe 64 flow from distributors 40A–C and down through the bed, bacteria in the bed consumes nutrients carried by the liquids and begins the clarification of the liquid. As liquid is drawn from below the floating bed and circulated to the top of the bed in sequence through one circulating system after another as described above, the untreated wastewater and leachate initially introduced through pipe 64 gradually migrates through the bed towards the outlet end of the vessel. In the course of this transit it is itself contacted by the bacteria in the bed and is treated just as the solid waste is treated in its transit from the inlet end to the outlet end of the vessel. Accordingly, the liquid in the tank 10 is treated along with the solids in that an untreated liquid is introduced at the inlet end (adjacent end wall 18) of the tank whereas a treated liquid is removed through opening 28 at the outlet end.

Gasses generated by the digestion process collect in the headspace 51 above the floating bed and are removed through the pipe 49. This gas can be burned off or used as a fuel to heat the influent water as needed to provide the proper temperature environment for bacteria growth within the vessel.

While the invention has been described in the context of a process for treating solid vegetable wastes from food processing operations, it should be appreciated that the process and apparatus of the present invention can be used for the anaerobic digestion of other organic material. It also is possible to include in the floating bed a quantity of inert material such as a low-density plastic. Such material can assist in the flotation of the bed. They also provide floating sites for attachment of the anaerobic microorganisms to facilitate the biological treatment of liquid wastes as opposed to solid wastes.

Also, rather than removing only the residue of the anaerobic treatment from the bottom of the floating bed through a passage 28, it also is possible to remove an entire vertical slice of the floating bed taken adjacent the outlet end wall 20.

Accordingly, while the invention has been described in connection with a presently preferred embodiment, those skilled in the art will recognize that modifications may be made therein without departing from the true spirit and scope of the invention, which is intended to be defined solely by the appended claims.

Having described the invention in detail, what is claimed as new is:

1. A process for the biological treatment of organic waste comprising:
 a) contacting organic solids in a closed vessel with a liquid containing anaerobic microorganisms, the solids forming particles for supporting and entrapping the bacteria and the solids being digested by the microorganisms and being buoyed in the liquid by the gases generated during such digestion so as to form a floating bed wherein an upper stratum of the bed contains the least digested and least dense material and a lower stratum of the bed contains the most digested and densest material;
 b) circulating liquid from beneath the floating bed to the upper surface of the floating bed and allowing the liquid to percolate down through the bed;
 c) moving the floating bed from an inlet end of the vessel to an opposite outlet end of the vessel; and
 d) removing the most digested, most dense material from the vessel at the outlet end.

2. A process as in claim 1 wherein said circulating of liquid comprises:
 a) drawing liquid from beneath the floating bed and introducing the liquid into the bed through a plurality of discharge ports located above the top surface of the floating bed;
 b) the introducing of liquid being in sequence through the discharge ports followed by a quiescent period and a portion of the floating bed in the immediate vicinity of each discharge port expanding downwardly during the introducing of liquid and thereafter compacting upwardly by floating and reforming back at its original level during the quiescent period; and
 c) said downward expanding and upward compacting bringing the microorganisms in the liquid into contact with the organic particles to promote biological degradation of the organic material and liberating gases from the bed.

3. A process as in claim 2 wherein the discharge ports are in series and the liquid is continuously introduced into the bed by sequencing the flow from one discharge port to another and the flow at one of the discharge ports commencing prior to the termination of flow and the start of the quiescent period at another of the discharge ports such that each individual port experiences a period of flow followed by a quiescent period.

4. A process as in claim 2 comprising introducing a wastewater stream into the liquid being circulated from below the floating bed to the upper surface of the floating bed.

5. A process as in claim 2 wherein said circulating liquid from beneath the floating bed to the upper surface of the bed comprises:
   a) drawing liquid from beneath the floating bed and introducing it over the upper surface of a first portion of the bed for a first period of time; and
   b) drawing liquid from beneath the floating bed and introducing it over the upper surface of a second portion of the bed for a second period of time.

6. A process as in claim 5 comprising overlapping the end of the first period of time and the start of the second period of time.

7. A process as in claim 5 wherein said first and second portions of the floating bed are adjacent portions that extend substantially the full length of the vessel.

8. A process as in claim 7 wherein introducing the liquid over the first and second portions of the bed occurs simultaneously over a plurality of spaced locations extending along the first and second portions.

9. A process as in claim 1 wherein moving the floating bed from an inlet end of the vessel to an opposite outlet end of the vessel is in part accomplished by the removing of the most digested, most dense material from the vessel at the outlet end.

10. A process as in claim 9 wherein removing the most digested, most dense material from the vessel at the outlet end comprises flushing a portion of the bed at the outlet end through an opening adjacent a lower portion of the outlet end.

11. A process as in claim 10 wherein flushing comprises:
   a) stopping the circulating of liquid from beneath a portion of the floating bed adjacent the outlet end of the vessel;
   b) opening a passage at a lower portion of the outlet end; and
   c) introducing a second liquid over a surface of the floating bed adjacent the outlet end, the quantity of the second liquid so introduced being sufficient to downwardly expand and flush a portion of the most digested, most dense material of the floating bed adjacent the outlet end through the passage.

12. A process as in claim 11 comprising collecting the portion of the floating bed flushed through the passage and separating the solid and liquid fractions of the flushed portion.

13. A process as in claim 11 wherein the second liquid includes liquid drawn from a reservoir containing the liquid fraction separated from the flushed portion.

14. A process according to claim 1 wherein the floating bed of support particles includes particles of an inert material.

15. A process for the biological treatment of organic wastes in a vessel containing a floating bed of support particles having attached and entrapped anaerobic microorganisms in an upper zone of the vessel comprising:
   a) introducing a liquid containing from 100% to 0% untreated wastewater at an inlet end of the vessel, the wastewater containing an organic waste;
   b) drawing the liquid from beneath the floating bed and introducing it over the bed through one of a plurality of discharge ports disposed above a top surface of the bed;
   c) discharging the liquid in a sequential manner first from one discharge port and then through an adjacent discharge port, a portion of the floating bed under each discharge port downwardly expanding in response to the weight of liquid discharged onto the bed;
   d) following each introduction of liquid with a quiescent period to allow the downwardly expanded portion of the bed to compact by floating and reforming back at its original level;
   e) passing the liquid downwardly through the bed and treating the wastewater therein during such passage by allowing the anaerobic microorganisms to biologically degrade and digest any organic content of the wastewater with gasses being generated by such digestion rising through the bed to buoy the support particles and accumulate in a head space above the floating bed, the action of the downwardly expanding and upwardly compacting of the bed acting to distribute the microorganisms through out the bed and promote the release of gases from the bed;
   f) removing treated waste water from below the floating bed at an outlet end of the vessel opposite the inlet end; and
   g) discharging the generated gases from a head space above the floating bed.

16. A process as in claim 15 wherein said support particles comprise organic solids and said microorganisms acting to digest said organic solids such that the floating bed has an upper stratum containing the least digested and least dense material and a lower stratum of the bed containing the most digested and densest; and periodically removing a portion of the lower stratum from the vessel.

17. A process as in claim 16 including moving the bed from the inlet end of the vessel to the outlet end and removing the most digested, most dense material from the vessel at the outlet end.

18. A process as in claim 17 wherein removing the most digested, most dense material comprises:
   a) opening a passage adjacent a lower portion of the outlet end; and
   b) flushing a portion of the bed adjacent the outlet end through the opening.

19. A process as in claim 18 wherein flushing comprises:
   a) stopping the drawing of liquid from beneath the floating bed adjacent the outlet end; and
   b) introducing a quantity of a second liquid over a surface of the floating bed adjacent the outlet end sufficient to downwardly expand and flush a portion of the most digested, most dense material of the floating bed adjacent the outlet end through the passage.

20. A process as in claim 19 wherein the second liquid is drawn from a stored supply of the treated waste water.

21. Apparatus for treatment of solid and liquid organic waste comprising;
   a) closed bioreactor containing a microorganism rich liquid for conducting the anaerobic digestion of organic matter, the vessel having an inlet end for introducing organic matter to be digested into the vessel and an outlet end for removing digested organic matter from the vessel, the organic matter forming a floating bed within the vessel having the densest most digested material in a lower stratum of the bed and the lightest least digested material in an upper stratum of the bed and
   b) means for withdrawing liquid from beneath the floating bed and sparging the liquid over the upper surface of the floating bed;

c) means for moving the floating bed from the inlet end to the outlet end; and d) means for removing the densest, most digested material from the vessel at the outlet end.

22. Apparatus as in claim 21 wherein said means for removing liquid from beneath said floating bed and discharging it over the surface of said floating bed includes a plurality of discharge ports arranged above the upper surface of the floating bed, the discharge ports being at spaced intervals extending from the inlet end to the outlet end and means for controlling the discharge of liquid through selected ones of the discharge ports in a sequential series of pulses, each of the pulses being followed by quiescent periods.

23. Apparatus as in claim 21 wherein said means for removing material from the vessel comprises:

a) a weir chimney exterior of the vessel including a passage for communicating the weir chimney with a lower portion of the vessel adjacent the outlet end, b) a pump for delivering a quantity of liquid to selected discharge ports located adjacent the outlet end sufficient to flush a portion of the floating bed from the vessel through the passage and into the weir chimney.

24. Apparatus as in claim 23 including a liquid-solids separator receiving the material flushed from the vessel for separating the flushed material into liquid and solid fraction and a reservoir for receiving the liquid fraction.

25. Apparatus as in claim 24 wherein said pump draws liquid from said reservoir for flushing a portion of the floating bed from the vessel.

* * * * *